(12) United States Patent
Yeom et al.

(10) Patent No.: US 6,544,873 B1
(45) Date of Patent: Apr. 8, 2003

(54) METHODS OF FABRICATING INTEGRATED CIRCUIT FIELD EFFECT TRANSISTORS INCLUDING MULTILAYER GATE ELECTRODES HAVING NARROW AND WIDE CONDUCTIVE LAYERS

(75) Inventors: Kye-hee Yeom, Kyungki-do (KR); Duck-hyung Lee, Kyungki-do (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 09/539,058

(22) Filed: Mar. 30, 2000

Related U.S. Application Data

(62) Division of application No. 08/853,806, filed on May 9, 1997.

(30) Foreign Application Priority Data

Jun. 7, 1996 (KR) .............................. 96/20358

(51) Int. Cl.[7] .......................................... H01L 21/3205
(52) U.S. Cl. ....................... 438/588; 438/216; 438/396; 438/592
(58) Field of Search ................................ 257/408, 412; 438/167, 216, 261, 287, 396, 785, 295, 296, 298, 303, 304

(56) References Cited

U.S. PATENT DOCUMENTS

| | | | |
|---|---|---|---|
| 4,440,841 A | * | 4/1984 | Tabuchi .......................... 430/5 |
| 4,605,947 A | | 8/1986 | Price et al. .................. 257/388 |
| 4,952,993 A | | 8/1990 | Okumura ..................... 257/388 |
| 5,034,791 A | * | 7/1991 | Kameyama et al. ........ 357/23.9 |
| 5,115,290 A | | 5/1992 | Murakami et al. .......... 257/388 |
| 5,384,479 A | | 1/1995 | Taniguchi .................... 257/412 |
| 5,411,903 A | * | 5/1995 | Wu et al. ....................... 437/41 |
| 5,471,080 A | | 11/1995 | Satoh et al. ................. 257/344 |
| 5,610,430 A | | 3/1997 | Yamashita et al. .......... 257/412 |
| 5,668,394 A | | 9/1997 | Lur et al. ..................... 257/413 |
| 5,801,427 A | | 9/1998 | Shiratake et al. ........... 257/413 |

* cited by examiner

Primary Examiner—Olik Chaudhuri
Assistant Examiner—Wai-Sing Louie
(74) Attorney, Agent, or Firm—Myers Bigel Sibley & Sajovec

(57) ABSTRACT

An integrated circuit field effect transistor includes a multilayer gate electrode having a first conductive layer and a second conductive layer on the first conductive layer, wherein the second conductive layer is wider than the first conductive layer. The first conductive layer may be formed of titanium nitride and the second conductive layer may be formed of tungsten, copper and/or titanium silicide. The first conductive layer may be recessed relative to the second conductive layer by wet etching using a solution of hydrogen peroxide or hydrogen peroxide and sulfuric acid.

10 Claims, 4 Drawing Sheets

(a) PRESENT INVENTION (b) PRIOR ART

METHODS OF FABRICATING INTEGRATED CIRCUIT FIELD EFFECT TRANSISTORS INCLUDING MULTILAYER GATE ELECTRODES HAVING NARROW AND WIDE CONDUCTIVE LAYERS

This is a division of application No. 08/853,806 filed May 9, 1997.

FIELD OF THE INVENTION

This invention relates to integrated circuit devices and fabrication methods therefor, and more particularly to integrated circuit field effect transistors and fabrication methods therefor.

BACKGROUND OF THE INVENTION

Integrated circuit field effect transistors are widely used in microelectronic devices including, but not limited to, microprocessors, logic devices and memory devices. As is well known to those having skill in the art, an integrated circuit insulated gate field effect transistor, often referred to as a MOSFET or MOS transistor, includes an insulated gate on the face of an integrated circuit substrate, between spaced apart source/drain regions in the integrated circuit substrate.

As the integration density of integrated circuits continues to increase, high performance gate electrodes for field effect transistors are desirable. In particular, it is generally desirable that the gate electrode material have low resistance and chemical stability, so as not to react with the gate insulating film during subsequent thermal treatments. The gate electrode material should also preferably have good adhesive strength so that it is not deformed by stress. Finally, it is preferred that the gate electrode material be readily etched in fine patterns to permit high device integration.

In order to meet at least some of these criteria, it has been proposed to form a multilayer gate electrode. In order to provide thermal stability and a good work function, it has been proposed to form a multilayer gate electrode including a first conductive layer of a metal nitride film such as titanium nitride (TiN) and a second conductive layer comprising a low resistance metal layer, on the first conductive layer. The low resistance metal layer may be, for example, a metal film comprising tungsten (W), titanium (Ti), titanium disilicide ($TiSi_2$) or copper (Cu).

The titanium nitride can provide an excellent diffusion barrier to reduce and preferably prevent diffusion from the low resistance metal layer into the gate oxide. Moreover, the work function of titanium nitride is almost the same as that of intrinsic silicon. Therefore, when the titanium nitride film is formed on the gate oxide film, complementary MOS transistors (referred to as "CMOS" transistors) can have a surface channel, to thereby improve the characteristics of the CMOS circuit.

FIG. 1 is a cross-sectional view of a conventional MOS transistor which uses a multilayer gate electrode. As shown in FIG. 1, a conventional MOS transistor includes a gate oxide film 102 on a face of an integrated circuit substrate such as a semiconductor substrate 100. A titanium nitride film 106 and a low resistance metal layer 108 such as a tungsten film, are formed on the gate oxide film 102 to provide a multilayer gate electrode.

Unfortunately, a conventional MOS transistor as described in FIG. 1 may encounter problems due to etching during fabrication thereof. In particular, in order to use the titanium nitride film 106 in the multilayer gate electrode, the etching selectivity between the titanium nitride film 106 and the gate insulating film 102 such as a silicon dioxide film, should be high. Unfortunately, it may be difficult to dry etch the device under these conditions. Accordingly, when dry etched, etching damage may occur in the gate oxide film under the edges of the gate electrode and in the semiconductor substrate under the gate oxide film. When this etching damage occurs, leakage current may flow between the gate electrode and the semiconductor substrate, thereby degrading the device characteristics.

It is known to use a thermal oxidation process to cure the gate oxide damage which may occur during the dry etch. Unfortunately, thermal oxidation may produce stress due to expansion, adjacent the titanium nitride film, and thereby may degrade the adhesion of the titanium nitride film.

A publication entitled "Novel Polysilicon/TiN Stacked-Gate Structure for Fully-Depleted SOI/CMOS" by Hwang et al., IEDM Technical Digest, International Electrode Devices Meeting, San Francisco, Calif., Dec. 13–16, 1992, pp. 345–348, describes an example of fabricating a gate electrode for a field effect transistor using wet etching. According to this publication, a very thin TiN layer (about 40 nm) was deposited by reactive sputtering on a 15-nm thermally-grown gate oxide, and was followed by deposition of a 300-nm thick polysilicon layer. A blanket phosphorus implant was used to dope the polysilicon. During the polysilicon gate etch, the underlying thin TiN layer serves as an excellent etch stop. The TiN was wetetched after formation of a 100-nm low-temperature oxide spacer. A second oxide spacer was then used to completely seal the exposed TiN edges.

Unfortunately, when a transistor is fabricated using wet etching as described above, it may be difficult to control the wet etching characteristics, such as etching uniformity and etching rates. Also, it may be difficult to form gate electrodes of uniform size due to isotropic etching. Moreover, the width of the bottom gate in the gate electrode which comprises titanium nitride, may be increased. The insulation margin with respect to the gate electrode may thereby be reduced, which may make it difficult to highly integrate the field effect transistor devices.

SUMMARY OF THE INVENTION

It is therefore an object of the present invention to provide improved integrated circuit field effect transistors and fabrication methods therefor.

It is another object of the present invention to provide integrated circuit field effect transistors which can produce surface channel devices having low leakage currents, and methods of fabricating same.

These and other objects are provided, according to the present invention, by integrated circuit field effect transistors including multilayer gate electrodes which comprise a first conductive layer and a second conductive layer on the first conductive layer, wherein the second conductive layer is wider than the first conductive layer. Stated differently, the first conductive layer is recessed relative to the second conductive layer. By providing narrow and wide gate electrode layers, wet etching can be performed to narrow the first conductive layer and thereby repair defects therein. An oxide spacer may then provide reduced leakage current and enhanced isolation, to thereby provide enhanced device characteristics.

In particular, according to the invention, an integrated circuit field effect transistor includes spaced apart source/drain regions in an integrated circuit substrate, at a face thereof. An insulating film is included on the face between the spaced apart source/drain regions. A gate electrode is included on the insulating film, between the spaced apart source/drain regions. The gate electrode comprises a first conductive layer on the insulating film, and a second conductive layer on the first conductive layer. The second conductive layer is wider than the first conductive layer. In particular, the second conductive layer extends beyond the first conductive layer towards the source/drain regions.

The first conductive layer preferably comprises titanium nitride and the second conductive layer is selected from the group consisting of tungsten, copper and titanium silicide. The insulating film preferably is thicker beneath the first conductive layer compared to outside the first conductive layer.

According to method aspects of the present invention, integrated circuit multilayer gate electrodes are fabricated by forming a first conductive layer on an integrated circuit substrate and forming a second conductive layer on the first conductive layer. The second and first conductive layers are then patterned to form a multilayer gate electrode such that the patterned second conductive layer is wider than the patterned first conductive layer.

The patterning step is preferably performed by wet etching the first conductive layer. The first conductive layer is preferably formed on an insulating film on an integrated circuit substrate. After patterning the second and first conductive layers, a sidewall spacer is preferably formed on the ends of the patterned first and second conductive layers.

When the first conductive layer comprises titanium nitride and the second conductive layer is selected from the group consisting of tungsten, copper and titanium silicide, the wet etching step may use an etching solution comprising hydrogen peroxide, and more preferably an etching solution comprising hydrogen peroxide and sulfuric acid. The etching solution may comprise six parts hydrogen peroxide and one part sulfuric acid.

Integrated circuit field effect transistors are formed, according to the present invention, by forming on an integrated circuit substrate, an insulating film, and a multilayer gate electrode comprising a first conductive layer on the insulating film and a second conductive layer on the first conductive layer. Ions are implanted into the integrated circuit substrate using the multilayer gate electrode as a mask, to form spaced apart first source/drain regions in the integrated circuit substrate. The first conductive layer is wet etched so that it is recessed relative to the second conductive layer. A sidewall spacer is formed on the ends of the first and second conductive layers. Ions are implanted into the integrated circuit substrate using the sidewall spacer as a mask, to form spaced apart second source/drain regions of higher doping concentration than the first source/drain regions. The sidewall spacer may comprise silicon dioxide, silicon nitride or combinations of silicon dioxide and silicon nitride. High performance multilayer gate electrode integrated circuit field effect transistors are provided thereby.

DETAILED DESCRIPTION OF PREFERRED EMBODIMENTS

Figure 1:
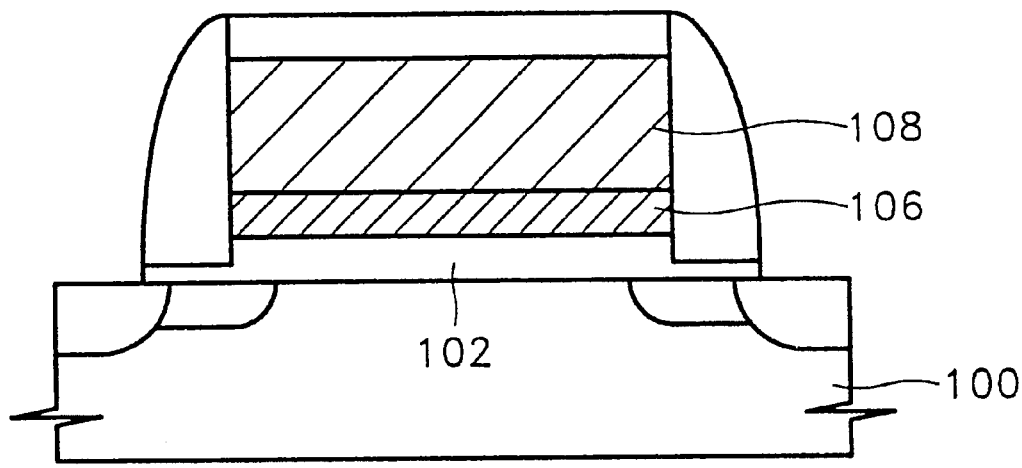
FIG. 1 is a cross-sectional view of a conventional integrated circuit field effect transistor.

The present invention now will be described more fully hereinafter with reference to the accompanying drawings, in which preferred embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art. In the drawings, the thickness of layers and regions are exaggerated for clarity. Like numbers refer to like elements throughout. It will also be understood that when a layer is referred to as being "on" another layer or substrate, it can be directly on the other layer or substrate, or intervening layers may also be present. Moreover, each embodiment described and illustrated herein includes its complementary conductivity type embodiment as well.

Figure 2:
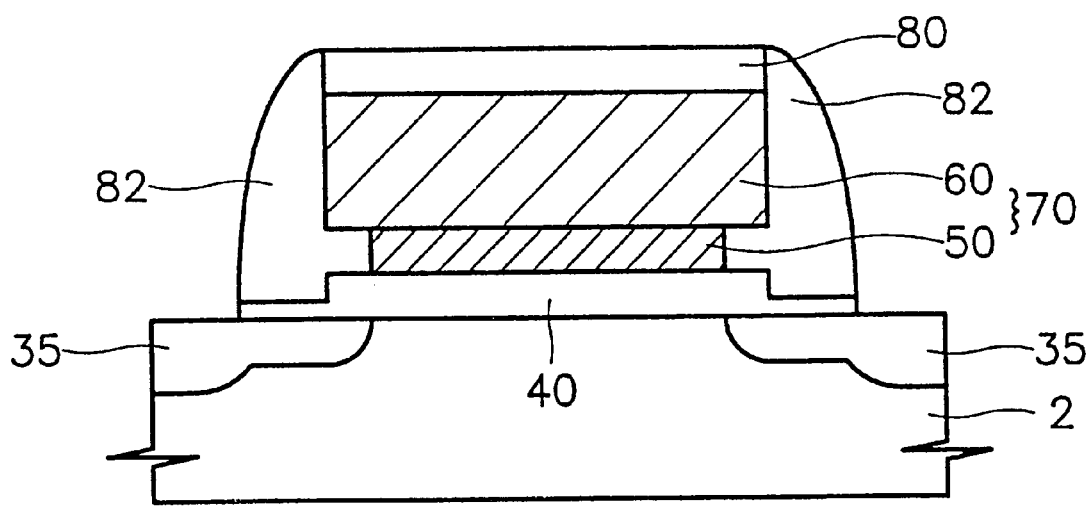
FIG. 2 is a cross-sectional view of an integrated circuit field effect transistor according to the present invention.

Referring now to FIG. 2, an integrated circuit field effect transistor according to the present invention will now be described. As shown in FIG. 2, the integrated circuit field effect transistor includes an integrated circuit substrate such as a semiconductor substrate 2, and spaced apart source/drain regions 35 in the semiconductor substrate 2 at a face thereof. As is well known to those having skill in the art, the spaced apart source/drain regions 35 define a channel region (not illustrated) therebetween.

Still referring to FIG. 2, a gate insulating film 40 is included on the face, between the spaced apart source/drain regions 35. The gate electrode 70 is included on the gate insulating film 40. A gate electrode 70 is a multilayer gate electrode including a first conductive layer 50 and a second conductive layer 60 which is wider than the first conductive layer 50. Stated differently, the first conductive layer 50 is recessed relative to the second conductive layer 60. In particular, the second conductive layer 60 extends beyond the first conductive layer 50 towards the source/drain regions. Stated another way, the second conductive layer extends beyond the first conductive layer in a first direction, for example to the left in FIG. 2, and extends beyond the first conductive layer in a second direction which is opposite the first direction, for example to the right in FIG. 2.

Finally, continuing with the description of FIG. 2, an insulating layer 80 is included on the multilayer gate electrode 70. Sidewall spacers 82 are also included on the ends of the first and second conductive layers. The first conductive layer 50 preferably comprises titanium nitride. The second conductive layer preferably is selected from the group consisting of tungsten, copper and titanium silicide.

Figure 3:
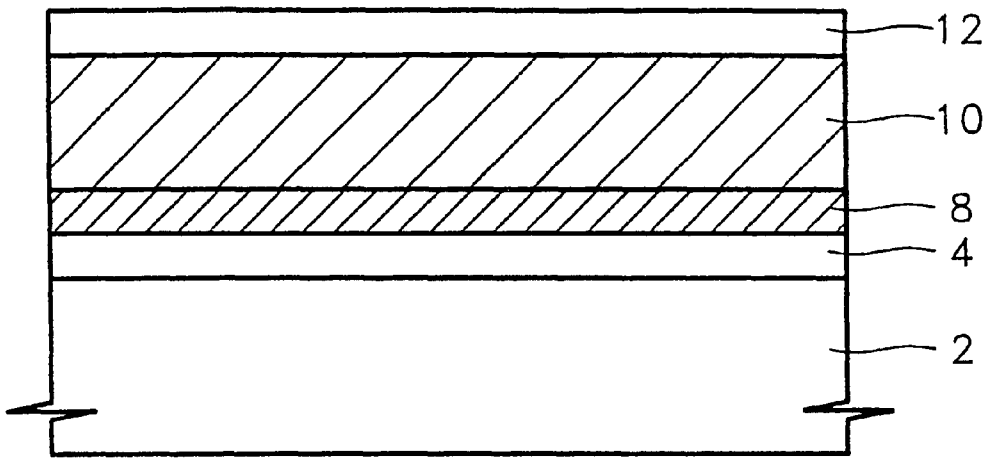
FIGS. 3–6 are cross-sectional views illustrating the field effect transistor of FIG. 2 during intermediate fabrication steps.

FIGS. 3–6 are cross-sectional views of the integrated circuit field effect transistor of FIG. 2 during intermediate fabrication steps. As shown in FIG. 3, a gate insulating film 4 such as a silicon dioxide film, is formed on an integrated circuit substrate such as a semiconductor substrate 2. Then, a first conductive layer 8, a second conductive layer 10 and a first insulating layer 12 are sequentially formed on one another. The first conductive layer 8 is preferably a titanium nitride film which is sufficiently thick to prevent diffusion, i.e. equal to or greater than about 300 Å. First conductive layer 8 is also preferably small enough so that it can be readily etched. In particular, first conductive layer 8 is preferably less than or equal to about 1000 Å in thickness.

The second conductive layer 10 preferably comprises a material having a low resistance compared to the titanium nitride film of the first conductive layer 8. Accordingly, a tungsten film, a copper film or a titanium silicide film may be used.

The first insulating layer 12 may function as a protective layer to prevent the second conductive layer 10 from being exposed and damaged by chemical reactions during subsequent processing. First insulating layer 12 may comprise a silicon dioxide, silicon nitride or other insulator.

Figure 4:
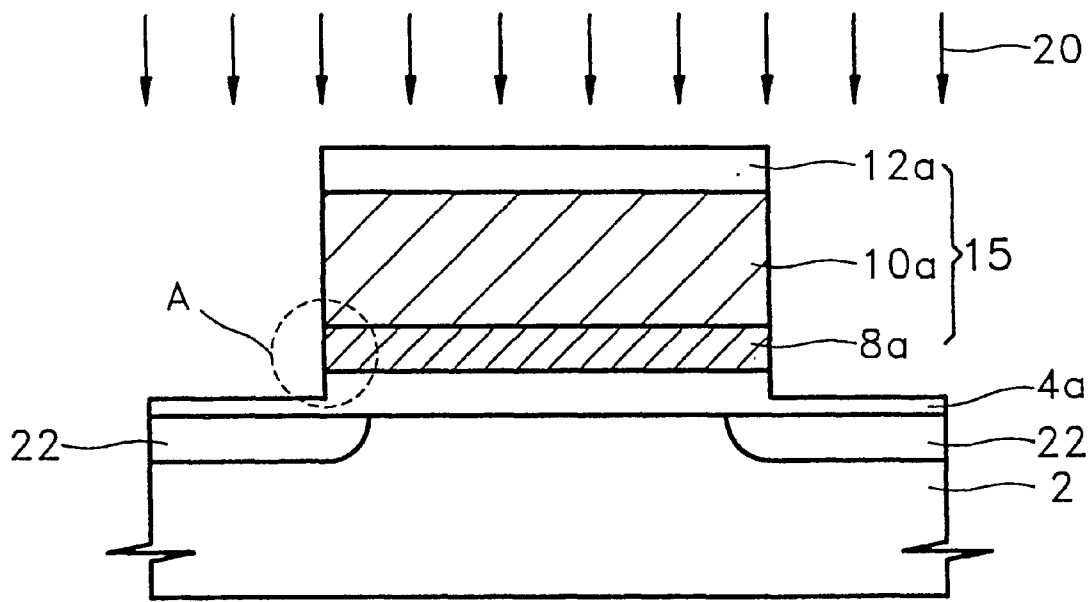

As shown in FIG. 4, the first and second conductive layers are patterned. A photoresist pattern (not shown in FIG. 4) is formed on the first insulating layer 12. The first insulating layer 12 is then etched using the photoresist as an etching mask, to thereby form a patterned first insulating layer 12a. After the photoresist film is removed, the second conductive layer 10 and the first conductive layer 8 are etched using the first patterned insulating layer 12a as an etch mask, to thereby form patterned second conductive layer 10a and patterned first conductive layer 8a. Thus, the gate pattern 15 includes patterned layers 12a, 10a and 8a.

It will be understood by those having skill in the art that a portion of the gate insulating film 4 may be damaged during the etching, to thereby produce a gate insulating film 4a which has a stepped portion A. Stated differently, the gate insulating film is thicker under gate electrode 8a compared to outside of gate electrode 8a.

Still referring to FIG. 4, ions 20 are implanted into the integrated circuit substrate using the multilayer gate electrode as a mask, to form spaced apart first source/drain regions 22 in the integrated circuit substrate. It will be understood by those having skill in the art that ions 20 are implanted to form lightly doped drain (LDD) structures. Doping concentrations of between $10^{16}$ and $10^{18}/cm^3$ may be used.

Figure 5:
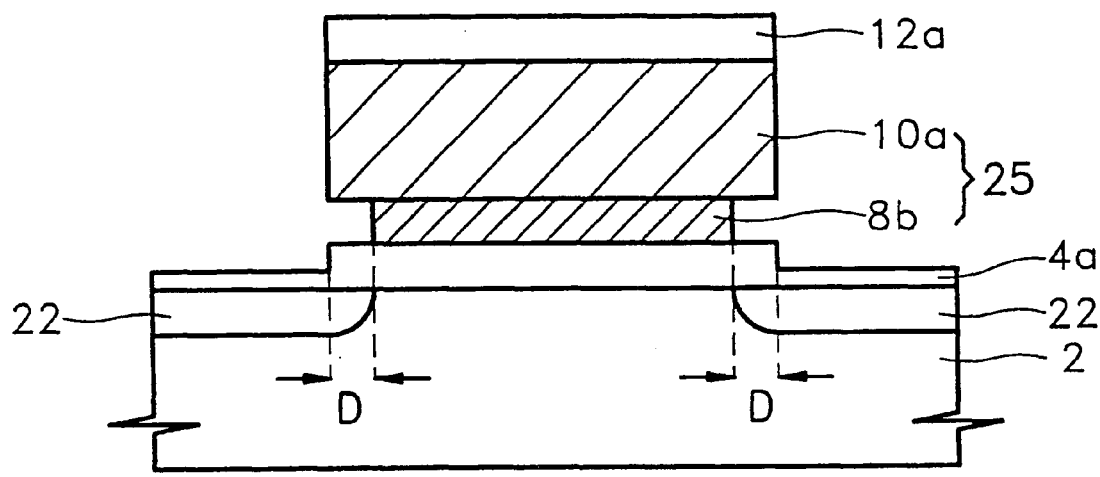

Referring now to FIG. 5, the patterned first conductive layer is wet etched so that it is recessed relative to the patterned second conductive layer. In particular, the sidewall of the patterned first conductive layer 8a is wet etched to a predetermined width D, preferably about 50–100 Å, to thereby form a further patterned first conductive layer 8b. Accordingly, the gate electrode 25 is formed by the conductive layers 10a and 8b. As shown in FIG. 5, the sidewall of the further patterned first conductive layer 8b is isolated from the stepped portion A of the gate insulating film 4a by a predetermined width D. Thus, the sidewall of the further patterned first conductive layer 8b preferably does not contact the damaged portion of the gate insulating layer in the stepped portion A. Since stresses at the edges of the further patterned first conductive layer 8b are not applied to the step portion of the insulator A, damage in the step portion A can be reduced and preferably prevented.

Still continuing with the description of FIG. 5, hydrogen peroxide or a mixed solution of hydrogen peroxide and sulfuric acid can be used as an etching solution to wet etch the sidewall of the patterned first conductive layer pattern 8a. When a mixed solution of hydrogen peroxide and sulfuric acid is used as an etching solution, it is preferable that the hydrogen peroxide and the sulfuric acid are mixed in a volume ratio of six to one.

When using such an etching solution, the etch rate of the titanium nitride film in the first conductive layer is approximately 200 Å/min. at a temperature of 130° C. Thus, when the sidewall of the patterned first conductive layer 8a is etched for about 20–30 seconds under the above-described conditions, a thickness D of between 50–100 Å is etched. Moreover, when the patterned second conductive layer 10a is formed of tungsten, the etch rate thereof is about one third the etch rate of the titanium nitride film. Thus, the width of the patterned second conductive layer 10a is not reduced significantly during the wet etching.

Finally, when the sidewall of the patterned first conductive layer 8a is etched using hydrogen peroxide or hydrogen peroxide and sulfuric acid as described above, the silicon layer or silicon dioxide is generally not etched by this etching solution, so that additional damage to the gate oxide film need not occur. Rather, the etching solution can provide a cleaning effect to remove residue which remains after the sidewall of the patterned first conductive layer 8a is etched.

Figure 6:
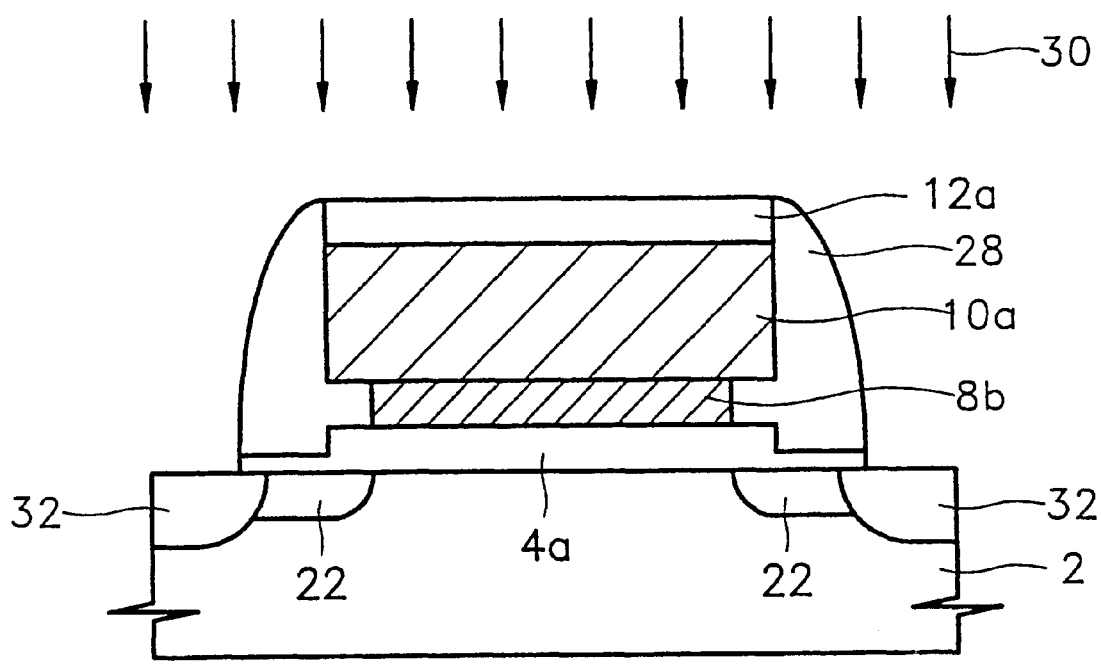

Referring now to FIG. 6, a sidewall spacer 28 is formed on the ends of the first and second conductive layers 8b and 10a, respectively. In particular, a second insulating layer is formed on the integrated circuit and is anisotropically etched, to thereby form the spacers 28 on the sidewalls of the first insulating layer 12a and the sidewalls of the first and second gate electrode layers 8b and 10a, respectively. The sidewall spacers may be formed of silicon dioxide, silicon nitride or combinations thereof and/or of other insulators. Finally, second ions 30 are implanted into the integrated circuit substrate using the sidewall spacer 28 as a mask, to form spaced apart second source/drain regions 32, of higher doping concentration than the first source/drain regions 22.

Figure 7:
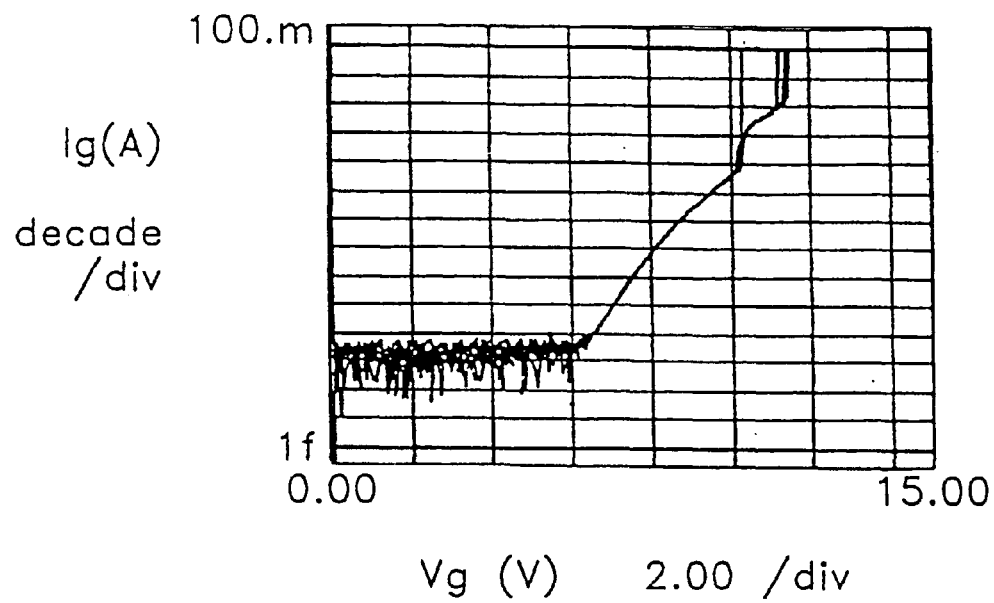
FIGS. 7(a)–7(b) graphically illustrate current (I) versus voltage (V) characteristics of an integrated circuit field effect transistor according to the present invention, and a conventional integrated circuit field effect transistor, respectively.
Figure 7:
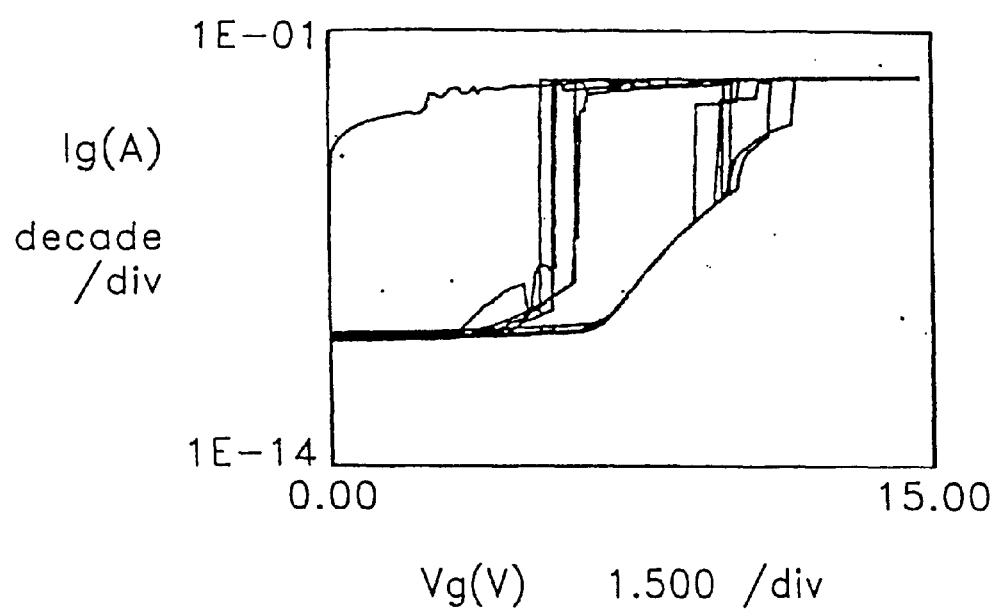

FIGS. 7(a) and 7(b) graphically illustrate the current (I) versus voltage (V) characteristics of gate oxide films of an integrated circuit field effect transistor according to the present invention and of a conventional integrated circuit field effect transistor, which omits the step of wet etching the first conductive layer, as shown in FIG. 1. The y axis represents leakage current $I_g$ and the x axis represents gate voltage $V_g$. As can be seen from FIG. 7(b), the gate insulating film may be destroyed at low voltages in many conventional integrated circuit field effect transistors. In contrast, as shown in FIG. 7(a), transistors according to the present invention can provide a relatively high breakdown voltage and a low leakage current as well. Accordingly, highly integrated field effect transistors may be provided with improved gate leakage current characteristics and breakdown voltages.

In the drawings and specification, there have been disclosed typical preferred embodiments of the invention and, although specific terms are employed, they are used in a generic and descriptive sense only and not for purposes of limitation, the scope of the invention being set forth in the following claims.

That which is claimed:

1. A method of fabricating an integrated circuit multilayer gate electrode, comprising the steps of:

forming an insulating film on an integrated circuit substrate;

forming a first conductive layer on the insulating film;

forming a second conductive layer on the first conductive layer; and patterning the second and first conductive layers and thinning the insulating film that is outside the second conductive layer to form a multilayer gate electrode such that the patterned second conductive layer is wider than the patterned first conductive layer and the insulating film is thicker beneath the second conductive layer compared to outside the second conductive layer;

wherein the patterning step comprises the step of wet etching the first conductive layer.

2. A method according to claim 1 wherein the patterning step is followed by the step of forming a sidewall spacer on the ends of the patterned first and second conductive layers.

3. A method according to claim 1:

wherein the step of forming a first conductive layer comprises the step of forming a first conductive layer comprising titanium nitride;

wherein the step of forming a second conductive layer comprises the step of forming a second conductive layer which is selected from the group consisting of tungsten, copper and titanium silicide; and wherein the wet etching step comprises the step of wet etching in an etching solution comprising hydrogen peroxide.

4. A method according to claim 3 wherein the wet etching step comprises the step of wet etching in an etching solution comprising hydrogen peroxide and sulfuric acid.

5. A method of fabricating an integrated circuit field effect transistor comprising the steps of:

forming on an integrated circuit substrate, an insulating film, and a multilayer gate electrode comprising a first conductive layer on the insulating film and a second conductive layer on the first conductive layer;

implanting ions into the integrated circuit substrate using the multilayer gate electrode as a mask, to form spaced apart first source/drain regions in the integrated circuit substrate;

wet etching the first conductive layer so that it is recessed relative to the second conductive layer;

forming a sidewall spacer on the ends of the first and second conductive layers; and implanting ions into the integrated circuit substrate using the sidewall spacer as a mask, to form spaced apart second source/drain regions of higher doping concentration than the first source/drain regions.

6. A method according to claim 5:

wherein the step of forming a first conductive layer comprises the step of forming a first conductive layer comprising titanium nitride;

wherein the step of forming a second conductive layer comprises the step of forming a second conductive layer which is selected from the group consisting of tungsten, copper and titanium silicide; and wherein the wet etching step comprises the step of wet etching in an etching solution comprising hydrogen peroxide.

7. A method according to claim 6 wherein the wet etching step comprises the step of wet etching in an etching solution comprising hydrogen peroxide and sulfuric acid.

8. A method according to claim 7 wherein the wet etching step comprises the step of wet etching in an etching solution comprising six parts hydrogen peroxide to one part sulfuric acid.

9. A method according to claim 5 wherein the sidewall spacer forming step comprises the step of forming a silicon dioxide or silicon nitride sidewall spacer.

10. A method according to claim 5 wherein the step of forming an insulating film and a multilayer gate electrode comprises thinning the insulating film that is outside the second conductive layer such that the insulating film is thicker beneath the second conductive layer compared to outside the second conductive layer.

* * * * *

UNITED STATES PATENT AND TRADEMARK OFFICE
CERTIFICATE OF CORRECTION

PATENT NO.   : 6,544,873 B1
DATED        : April 8, 2003
INVENTOR(S)  : Yeom et al.

It is certified that error appears in the above-identified patent and that said Letters Patent is hereby corrected as shown below:

<u>Title page,</u>
Item [56], References Cited, OTHER PUBLICATIONS, the following reference should be listed:

-- Hwang et al., *Novel Polysilicon/TiN Stacked-Gate Structure for Fully-Depleted SOI/ CMOS*, IEDM Technical Digest, International Electrode Devices Meeting, San Francisco, CA December 13-16, 1992, pp. 345, 348. --

Signed and Sealed this

Second Day of March, 2004

JON W. DUDAS
*Acting Director of the United States Patent and Trademark Office*